United States Patent [19]

Aretz et al.

[11] Patent Number: 4,990,444
[45] Date of Patent: Feb. 5, 1991

[54] GAMMA-GLUTAMYLTRANSPEPTIDASE, ITS PREPARATION AND ITS USE

[75] Inventors: Werner Aretz, Königstein/Taunus; Klaus Sauber, Schwalbach am Taunus, both of Fed. Rep. of Germany

[73] Assignee: Hoechst Aktiengesellschaft, Frankfurt am Main, Fed. Rep. of Germany

[21] Appl. No.: 144,338

[22] Filed: Jan. 15, 1988

[30] Foreign Application Priority Data

Jan. 17, 1987 [DE] Fed. Rep. of Germany ....... 3701221

[51] Int. Cl.$^5$ .......................... C12Q 1/48; C12N 1/20; C12N 9/10
[52] U.S. Cl. ......................................... 435/15; 435/24; 435/193; 435/253.3; 435/252.2
[58] Field of Search ................... 435/15, 24, 193, 875, 435/877, 830, 873, 839, 874, 253.3, 252.1, 252.2

[56] References Cited

PUBLICATIONS

Szewcyuk et al., Chemical Abstracts, 67:29395b, p. 2766 (1967).
Petrus et al., Chemical Abstract, 78:13104x, p. 157 (1973).
Kinchi et al., Chemical Abstracts, 104:202744x, p. 340 (1986).
Barthelemy et al., Chemical Abstracts, 89:18968u; p. 234 (1978).
Hara et al., Chemical Abstracts, 97:178535u, p. 467 (1982).
ATCC Catalogue of Bacteria, Phages, rRNA Vectors, 16th Edition, p. 143 (1985).

*Primary Examiner*—Esther L. Kepplinger
*Assistant Examiner*—Laurie A. Scheiner
*Attorney, Agent, or Firm*—Finnegan, Henderson, Farabow, Garrett, and Dunner

[57] ABSTRACT

It is possible with the aid of a γ-glutamyltranspeptidase, which can be prepared by fermentation, to hydrolyze adipinyl- or glutaryl-monoamino compounds, in particular α-keto-adipinyl- or glutaryl-7-aminocephalosporanic acid.

2 Claims, No Drawings

γ-GLUTAMYLTRANSPEPTIDASE, ITS PREPARATION AND ITS USE

In animal tissues and in microorganisms, γ-glutamyl-transpeptidases (γ-GTP hereinafter) play an important part in amino acid metabolism and in the glutathione cycle [Meth. Enzymol. 77, 237 (1981)]. They are responsible for the transport of various amino acids in the form of their γ-glutamyl derivatives, for the formation of polyglutamic acid in Bacilli and for the breakdown of glutathione (γ-glutamyl-cysteinyl-glycine).

It has now been found, surprisingly, that some microorganisms synthesize γ-GTP with the aid of which it is possible, apart from the abovementioned reactions, to hydrolyze adipinyl- or glutaryl-monoamino compounds as well.

Hence the invention relates to

1. A γ-glutamyltranspeptidase (γ-GTP) which can be obtained by fermentation of bacteria and, furthermore, has the following characteristics
   a molecular weight of 20,000 to 60,000
   an isoelectric point of pH 5.0 to 6.5
   a pH optimum of 6.5 to 10 with
   L-glutamyl p-nitroanilide as substrate a $K_m$ of 9 to 36 μM at pH 8. 2. The process for the preparation of the γ-GTP defined under 1, which comprises cultivation of bacteria in a nutrient medium until the enzyme accumulates. 3. The use of the γ-GTP defined under 1 for the enzymatic hydrolysis of adipinyl- or glutaryl-monoamino compounds.

The invention, especially its preferred embodiments, is described in detail hereinafter. The invention is also defined in the patent claims.

The γ-glutamyltranspeptidase (γ-GTP) according to the invention catalyzes the hydrolysis of glutaryl- or adipinyl-monoamino compounds, for example those of the general formula

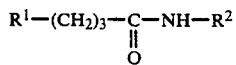

in which $R^1$ denotes a carboxyl, a carboxycarbonyl

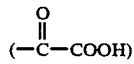

or a carboxymethyl group, and $R^2$ denotes residues of amino acids, dipeptides, cephems, cephams or derivatives thereof, to give the corresponding acid and the monoamino compound. 7-Aminocephalosporanic acid derivatives are preferably used as substrate, in particular α-keto-adipinyl- or glutaryl-7-aminocephalosporanic acid.

The enzyme product is found in the periplasmic space of microorganisms and may be characterized by a molecular weight of 20,000 to 60,000, preferably 23,000 to 40,000, in particular 30,000 to 35,000, and by an isoelectric point which is at a pH of 5.0 to 6.5, preferably 5.7 to 6.1. The pH optimum of the enzyme product is in the pH range 6.5 to 10 with L-γ-glutamyl paranitroanilide as substrate. The $K_m$ of the transpeptidase according to the invention for the same substrate is 9 to 36 μM, preferably 15 to 20 μM, in particular 8.1 μM, at pH 8.

The γ-GTP according to the invention is irreversibly inhibited in the presence of azaserine or iodoacetamide. The enzyme is found to be reversibly inhibited in the presence of copper, mercury and a mixture of serine and borate, as well as in the presence of 7-aminocephalosporanic acid.

The preparation is carried out with the aid of microorganisms. Screening revealed bacteria, in particular the genera Pseudomonas, Proteus, Arthrobacter and Bacillus, which provide good yields of the γ-GTP according to the invention; suitable and preferred examples are:

Pseudomonas putida ATCC 17390, Pseudomonas aeruginosa NCTC 10701, Proteus vulgaris ATCC 9634, Arthrobacter parafineus ATCC 21317 and Pseudomonas fragi DSM 3881 and Bacillus subtilis IFO 3025. The enzyme is particularly preferably obtained from Pseudomonas fragi DSM 3881. Mutants and variants of the said microorganisms are also suitable.

The microorganisms are cultured aerobically, singly or in mixed cultures, for example submerged with shaking or stirring in shaken flasks or fermenters, where appropriate with the introduction of air or oxygen. The fermentation can be carried out in a temperature range of about 20° to 37° C., preferably at about 25° to 30° C., in particular at 28° to 30° C. Fermentation is carried out in a pH range between 5 and 8.5, preferably between 5.5 and 8.0. Under these conditions, detectable accumulation of the enzyme in the culture broth is generally found after 1 to 3 days. The synthesis of γ-GTP starts in the late log phase and reaches its maximum in the stationary phase of growth. The production of the periplasmic enzyme can be followed with the aid of activity assays by HPLC analysis or photometry.

The nutrient solution used for the production of γ-GTP contains 0.2 to 5%, preferably 0.5 to 2%, of organic nitrogen compounds, as well as inorganic salts. Suitable organic nitrogen compounds are: amino acids, peptones, also meat extracts, round seeds, for example of corn, wheat, beans, soybean or the cotton plant, distillation residues from the production of alcohol, meat meals or yeast extracts. Examples of inorganic salts which the nutrient solution may contain are chlorides, carbonates, sulfates or phosphates of the alkali metals or alkaline earth metals, iron, zinc and manganese, as well as ammonium salts and nitrates.

Addition of assimilable carbohydrates increases the yield of biomass. Carbohydrates are also added in the abovementioned concentrations. Examples of preferred sources of carbon which can be added to the nutrient solution are sugars, such as glucose or sucrose, as well as carbohydrate-containing natural products, such as malt extract.

Although the optimum fermentation conditions differ for each microorganism, they are either already known to the expert or can be established in simple preliminary tests.

Purification can be carried out by classical processes via lysozyme digestion, ammonium sulfate precipitation and ion exchange and gel permeation chromatography. The enzyme can be coupled by conventional methods (Colowick and Kaplan, Meth. Enzymol., vol. XLIV)

It is possible to use for the enzymatic reaction not only whole cells in free or immobilized form, with the addition of β-lactamase inactivators, for example clavulanic acid or thienamycin, but also the isolated enzyme product, which can also be carrier-bound. Examples of suitable materials for the immobilization of whole cells are chitosan, alginate, χ-carrageenan, polyacrylohydrazides and other known substances from processes known from the literature (K. Venkatsubramanian, Immob. Cells (1979), ACS Symposium Series, p. 106).

The γ-GTP according to the invention has industrial importance, especially for obtaining 7-aminocephalosporanic acid from cephalosporin C, in particular since disclosure of a yeast, namely Trigonopsis variabilis (German Offenlegungsschrift 2,219,454) with whose aid it is possible to produce high yields of glutaryl-7-aminocephalosporanic acid from cephalosporin C. This compound can now be hydrolyzed with γ-glutamyl-transpeptidase to give good yields of 7-aminocephalosporanic acid. This closes a gap in the enzymatic breakdown of cephalosporin C to 7-aminocephalosporanic acid, which is industrially important for the semisynthetic cephalosporins.

A further description of the invention is given in the examples which follow. Unless otherwise indicated, percentage data relate, as they do in the previous description, to weight.

EXAMPLE 1

The γ-GTP-producing microorganism strains are maintained on agar slants of the following composition:

| | |
|---|---|
| Glucose | 1% |
| Casein-peptone | 0.4% |
| Meat extract | 0.4% |
| Yeast extract | 0.05% |
| Liver extract | 0.05% |
| NaCl | 0.25% |
| pH 7.2 | |

The slants are incubated at 28° C. for 2 days. The cells are then rinsed off with 10 ml of physiological saline, and 1 ml of this suspension is used to inoculate a 50 ml preculture of the following composition in a 300 ml capacity Erlenmeyer flask:

| | |
|---|---|
| Peptone | 1% |
| Malt extract | 0.5% |
| pH 7.0 | |

The flask is incubated at 30° C. in a rotary shaker at 190 rpm for 24 hours. 2.5 ml of this culture are used to inoculate 50 ml of main culture:

| (A) Gram-negative bacteria | | (B) Bacilli | |
|---|---|---|---|
| Peptone | 1% | Peptone | 0.12% |
| Meat extract | 0.5% | Yeast extract | 0.12% |
| NaCl | 0.5% | Glucose | 0.25% |
| $KH_2PO_4$ | 0.1% | Na lactate (60%) | 5.6 ml |
| $K_2HPO_4$ | 0.1% | $NH_4Cl$ | 0.12% |
| $MgSO_4 \times 7H_2O$ | 0.05% | $K_2HPO_4$ | 0.12% |
| pH 7.0 | | $KH_2PO_4$ | 0.034% |
| | | $MgSO_4 \times 7 H_2O$ | 0.025% |
| | | NaCl | 0.5% |
| | | KCl | 0.5% |
| | | $CaCl_2 \times 2 H_2O$ | 0.0015% |
| | | $MnCl_2 \times 4 H_2O$ | 0.0007% |
| | | $Fe(NH_4)$citrate | 0.00015% |

The culture is incubated at 28°C., shaking at 190 rpm, for 24 hours and is then harvested by centrifugation.

γ-GTP activities for some strains are listed in the table below:

| Strain | γ-GTP (mU/ml culture solution) |
|---|---|
| Ps. putida ATCC 17390 | 13 |
| Ps. aeruginosa NCTC 10701 | 11 |
| Proteus vulgaris ATCC 9634 | 26 |
| Arthrobacter parafineus ATCC 21317 | |
| Ps. fragi DSM 3881 | 37 |
| B. subtilis IFO 3025 | 31 |

EXAMPLE 2

A preculture of Ps. fragi DSM 3881 is cultured in analogy to Example 1. 50 ml of this culture are used to inoculate 2 l of main culture solution in a 5 l fermenter. The strain is cultured at 28° C. under an oxygen partial pressure of 70%. The γ-GTP production is followed by photometry, and the culture is harvested at the maximum enzyme titer. Under the said conditions, a γ-GTP titer of 50 mU/ml of culture solution is reached.

EXAMPLE 3

1 g of the cells obtained as in Example 2 is mixed with 2 ml of digestion buffer of the following composition:

20 mM TRIS 10 mM EDTA pH 7.6

12 mM $M_gSO_4 \times 7H_2O$

After preparation of the suspension, the following additions are made:

Lysozyme: 0.8 mg/ml

DNAse: 10 mg/ml, 30 μl of this in 1 ml of suspension.

The mixture is incubated at room temperature for 15 minutes. The lyzed cells are spun down at 30,000 xg. A 2% strength protamine sulfate solution is mixed, in a amount of 20% by volume, with the supernatant. The precipitate is removed by centrifugation and discarded. The supernatant is subjected to fractional precipitation with ammonium sulfate (50–80% saturation). The pellet is taken up, again, in 1/20 of the original volume, in 0.1 M citrate buffer, pH 5.0. A heat treatment (1 h, 37° C.) is then carried out, followed by centrifugation and dialysis against 20 mM citrate buffer, pH 5.0. The retentate is applied to a carboxymethylcellulose column. 6 ml of CM-cellulose 52 from Whatman are used for each ml of enzyme solution. The eluent used is 20 mM citrate buffer, pH 5.0, with a linear sodium chloride gradient (0 to 0.5 M).

The active fractions (HPLC assay) are dialyzed against 10 mM TRIS buffer, pH 8.0, and further purified on a DEAE-cellulose column (DE 52, Whatman). The eluent used is 20 mM TRIS buffer, pH 8.0, with a linear NaCl gradient (0 to 0.3 M).

The fraction with the highest activity (photometer assay) is used for subsequent investigations.

EXAMPLE 4

1 ml of an enzyme product prepared as in Example 3 is concentrated 5:1 and applied to a column of cross-linked agarose (®Superose 12, Pharmacia).
The mobile phase used is 50 mM potassium phosphate buffer, pH 7.0, containing 0.15 M NaCl. The pumping rate is 0.3 ml per minute. The γ-glutamyltranspeptidase is eluted with 15.4 ml of buffer. It can be detected using L-γ-glutamyl p-NO$_2$-anilide and the cleavage of glutaryl-7-aminocephalosporanic acid to 7-aminocephalosporanic acid. The molecular weight range of the γ-GTP corresponds to 30,000–35,000.

EXAMPLE 5

Biomass prepared as in Example 2 is worked up in analogy to Example 3, up to and including the heat treatment. Dialysis against 20 mM potassium phosphate buffer, pH 5.5, is then carried out. Carboxymethylcellulose (CM 52 from Whatman) is added to the retentate until the supernatant is lactamase-free. Dialysis against 10 mM TRIS, pH 8.0, is followed by chromatography on a DEAE-cellulose column (DE 52, Whatman) with four times the volume. The eluant used is 20 mM TRIS buffer, pH 8.0, plus a linear gradient of 0.1 M NaCl. The active fractions are found using the photometer assay, and then the enzyme is precipitated with 80% ammonium sulfate. The pellet is taken up in 50 mM potassium phosphate buffer, pH 7.0, and 0.15 M NaCl (concentrated 25:1).

Further purification is carried out on a column packed with a copolymer of dextran and acrylamide (®Sephacryl, Pharmacia). The column used for 3.5 ml of concentrate has the dimensions 2.5×82 cm. The eluting buffer is 50 mM potassium phosphate buffer, pH 7.0. The active fractions found using the HPLC assay are concentrated with ammonium sulfate. The pellet is taken up in 20 mM potassium phosphate buffer, pH 6.0.

EXAMPLE 6

The following mixture is chosen for preparative reaction of glutaryl-7-aminocephalosporanic acid:

100 μl of enzyme concentrate prepared as in Example 3, and

100 μl of 40 mM glutaryl-7-aminocephalosporanic acid, dissolved in 20 mM potassium phosphate buffer, pH 6.0, incubating at a temperature of 33° C.

Aliquots are removed every hour and examined by HPLC for the production of 7-aminocephalosporanic acid. 52% of the mixture has reacted after about 2.5 hours. Increasing the pH stepwise to 7.0 results in a maximum reaction of after a total of 8 hours.

EXAMPLE 7

Determination of γ-GTP activity (a) HPLC assay

50 μl of 80 mM glutaryl-7-aminocephalosporanic acid are mixed with 100 to 140 μl of 250 mM potassium phosphate buffer, pH 5.0, and 10 to 50 μl of enzyme solution, and the mixture is incubated at 33° C. 20 μl samples are taken every 10 minutes. The reaction is stopped with 20 μl of methanol. Centrifugation and dilution in the ratio of 1:10 with water are carried out. A 10 μl sample is examined by HPLC for the 7-aminocephalosporanic acid content. Stationary phase: C-18-silica gel Mobile phase: KH$_2$PO$_4$, 50 mM in H$_2$O, MeOH (80:20) + b 0.001% tetrabutylammonium sulfate.

(b) Photometric assay

600 μl of L-γ-glutamyl p-nitroanilide (166 μM) 300 μl of potassium phosphate buffer, pH 5.7, 50 mM and 100 μl of culture solution are mixed together and incubated at 37° C.

$$\epsilon_{405} = 9620 \frac{1}{mol \cdot cm}$$

We claim:

1. A method of hydrolyzing alpha-keto-adipinyl-or glutaryl-7-amino-cephalosporanic acid which comprises incubating alpha-keto-adipinyl- or glutaryl-7-amino-cephalosporanic acid with gamma-GTP which can be obtained by fermentation of bacteria and, furthermore, has the following characteristics a molecular weight range of 20,000 to 60,000 an isoelectric point of pH 5.0 to 6.5 a pH optimum of 6.5 to 10 with L-gamma-glutamyl paranitroanilide as substrate a $K_m$ of 9 to 36 microM at pH 8 the ability to hydrolyze adipinyl- or glutaryl-monoamino compounds.

2. Pseudomonas fragi DSM 3881 pl and its variants and mutants able to produce the γ-GTP which has the following characteristics:

(a) a molecular weight range of 20,000 to 60,000, (b) an isoelectric point of Ph 5.0 to 6.5, (c) a pH optimum of 6.5 to 10.0 with L-γ-glutamyl paranitroanilide as substrate, (d) a $K_m$ of 9 to 36 μM at pH 8.0, and (e) the ability to hydrolyze adipinyl- or glutaryl-monoamino compounds.

* * * * *

UNITED STATES PATENT AND TRADEMARK OFFICE
CERTIFICATE OF CORRECTION

PATENT NO. : 4,990,444

DATED : February 5, 1991

INVENTOR(S) : Werner Aretz et al.

It is certified that error appears in the above-identified patent and that said Letters Patent is hereby corrected as shown below:

Column 6, claim 2, line 1, delete "pl"; and
line 5, change "Ph" to --pH--.

Signed and Sealed this

Eleventh Day of January, 1994

Attest:

BRUCE LEHMAN

Attesting Officer    Commissioner of Patents and Trademarks